(12) United States Patent
Lim

(10) Patent No.: US 11,260,192 B2
(45) Date of Patent: Mar. 1, 2022

(54) RESPIRATORY MASK WITH NASOGASTRIC TUBE PATH

(71) Applicant: Fisher & Paykel Healthcare Limited, Auckland (NZ)

(72) Inventor: Jae Yun Lim, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/886,452

(22) Filed: May 28, 2020

(65) Prior Publication Data

US 2020/0289774 A1 Sep. 17, 2020

Related U.S. Application Data

(63) Continuation of application No. 15/114,377, filed as application No. PCT/NZ2015/050019 on Feb. 26, 2015, now Pat. No. 10,722,672.

(60) Provisional application No. 61/945,034, filed on Feb. 26, 2014.

(51) Int. Cl.
*A61M 16/06* (2006.01)
*A61J 15/00* (2006.01)
*A61M 16/08* (2006.01)
*A61M 16/04* (2006.01)

(52) U.S. Cl.
CPC ...... *A61M 16/0616* (2014.02); *A61J 15/0003* (2013.01); *A61J 15/0053* (2013.01); *A61M 16/0683* (2013.01); *A61M 16/0816* (2013.01); *A61M 16/0415* (2014.02); *A61M 16/0461* (2013.01); *A61M 2205/0216* (2013.01); *A61M 2205/583* (2013.01)

(58) Field of Classification Search
CPC ............. A61M 16/06; A61M 16/0605; A61M 16/0611; A61M 16/0616; A61M 16/0622; A61M 2016/0661; A61M 16/0461; A61J 15/0003; A61J 15/0053
See application file for complete search history.

(56) References Cited

U.S. PATENT DOCUMENTS

| 4,328,797 | A | 5/1982 | Rollins, III et al. |
| 8,869,797 | B2 * | 10/2014 | Davidson ............... A61M 16/06 |
| | | | 128/206.24 |
| 2003/0168063 | A1 | 9/2003 | Gambone |
| 2004/0244799 | A1 | 12/2004 | Landis |

(Continued)

FOREIGN PATENT DOCUMENTS

| EP | 1484075 | 12/2004 |
| WO | WO 2013/066195 | 5/2013 |

OTHER PUBLICATIONS

PCT Application No. PCT/NZ2015/050019 International Search Report and Written Opinion dated Apr. 13, 2015, in 9 pages.

*Primary Examiner* — Margaret M Luarca
*Assistant Examiner* — Cana A Gallegos
(74) *Attorney, Agent, or Firm* — Knobbe, Martens, Olson & Bear, LLP

(57) ABSTRACT

A respiratory mask can be used to provide therapy to patients who also require a nasogastric (NG) tube. The mask seal can include a path that is designed to deform around an NG tube or other without lifting the mask away from a patient's face. The deforming path can help to minimize gaps that form between the patient's face and the mask seal as a result of the tube, thus reducing leaks and improving the efficacy of the treatment.

28 Claims, 7 Drawing Sheets

(56) References Cited

U.S. PATENT DOCUMENTS

| | | |
|---|---|---|
| 2007/0107733 A1 | 5/2007 | Ho et al. |
| 2007/0267017 A1 | 11/2007 | McAuley et al. |
| 2008/0230072 A1 | 9/2008 | Rollins et al. |
| 2011/0088699 A1* | 4/2011 | Skipper ................. A61M 16/06 |
| | | 128/206.26 |
| 2011/0203591 A1 | 8/2011 | Amarasinghe |
| 2011/0265796 A1 | 11/2011 | Amarasinghe et al. |
| 2012/0285448 A1 | 11/2012 | Dugan et al. |
| 2012/0285464 A1 | 11/2012 | Birch |
| 2013/0192601 A1 | 8/2013 | Reischl et al. |
| 2013/0199537 A1* | 8/2013 | Formica ............. A61M 16/0611 |
| | | 128/205.25 |

* cited by examiner

RESPIRATORY MASK WITH NASOGASTRIC TUBE PATH

INCORPORATION BY REFERENCE TO ANY PRIORITY APPLICATIONS

Any and all applications for which a foreign or domestic priority claim is made are hereby incorporated by reference and made a part of the present disclosure.

BACKGROUND

Field

The present disclosure generally relates to respiratory masks, such as those intended for use in non-invasive ventilation (NIV). More particularly, the present disclosure relates to a seal or cushion for an NIV mask or other mask that enhances the sealing capabilities of the mask when used in combination with a tube, such as a nasogastric (NG) tube, a nasojejunal (NJ) tube and/or an oro-gastric (OG) tube, for example.

Description of Related Art

NIV masks commonly are used on patients who also require an NG, NJ and/or OG tube for feeding or delivery of medication. Traditionally, NIV masks are not designed for use in combination with an NG, NJ and/or OG tube and, as such, the efficacy of the NIV therapy can be compromised when such a combination is desired.

Traditional NIV masks have a silicone or thermoplastic elastomer (TPE) seal/cushion that conforms to a patient's face in order to create an air-tight seal. These cushions generally are flexible but not to an extent that allows the cushion to conform to very small features. In circumstances where an NG, NJ and/or OG tube is desired to be used in combination with an NIV mask, it is typical for the mask to be placed over the top of the tube(s). The tube(s) lift the cushion away from the patient's face, creating gaps around the tube that cause the seal to be broken and allow leaks to occur.

There are several techniques currently used to minimize gaps and to reduce leaks. These techniques include strapping the mask tighter onto the patient, using an adhesive pad to fill the gaps between the tube, cushion and patient's face, or passing the NG, NJ and/or OG tube through a port in the mask. Strapping the mask tighter can be uncomfortable for the patient and can lead to pressure-related skin damage. It also is possible that the NG, NJ and/or OG tube may be deformed by the tight fit of the mask and this could lead to blockages within the tube. The use of an adhesive pad creates extra work for the clinician who is fitting the NG tube or other tube and mask because it is another component that has to be fitted and aligned. In addition, the pad may not be successful in blocking the gaps effectively if the tube is too large or small or if the tube and/or the pad are misaligned. Passing the NG, NJ and/or OG tube through a port in the mask eliminates any breaks in the seal caused by the tube but often requires the tube to be removed in order to remove the mask. Removing and replacing NG, NJ and/or OG tubes can be uncomfortable and can cause irritation to the patient.

SUMMARY

The systems, methods and devices described herein have innovative aspects, no single one of which is indispensable or solely responsible for their desirable attributes. Without limiting the scope of the claims, some of the advantageous features will now be summarized.

Certain features, aspects and advantages of the embodiments include a respiratory mask with a cushion that is designed to accommodate an NG, NJ and/or OG tube passing between the mask and a patient's face. The cushion has specific thin regions that are designed to conform to the geometry of an NG, NJ and/or OG tube, which regions can help to reduce or minimize leak-causing gaps that might be otherwise created between the cushion and the patient's face.

In some configurations, a cushion for a respiratory mask includes a face contacting portion and at least one thin region at least partially within the face contacting portion. The thin region is adapted to accommodate the placement of a tube between the face contacting portion and a face of a user.

In some configurations, in use, the at least one thin region is adapted to conform to a shape of the tube while substantially maintaining an adequate seal with the face of the user.

In some configurations, the at least one thin region is located on a lateral side of the face contacting portion.

In some configurations, the at least one thin region comprises a thin region on each lateral side of the face contacting portion.

In some configurations, the thin region on one lateral side is a relatively larger thin region and the thin region on the other side is a relatively smaller thin region.

In some configurations, the at least one thin region comprises two or more thin regions on one lateral side of the face contacting portion. In some configurations, a first thin region and a second thin region of the two or more thin regions are spaced apart from one another. In some configurations, the first thin region and the second thin region are spaced apart along a perimeter of the face contacting portion. In some configurations, the two or more thin regions comprise at least one relatively larger thin region and at least one relatively smaller thin region.

In some configurations, the at least one thin region extends in a direction from an inner edge of the face contacting portion toward an outer edge of the face contacting portion.

In some configurations, the at least one thin region extends downwardly relative to a horizontal axis from an inner end portion to an outer end portion. In some configurations, the at least one thin region extends downwardly at an angle of between about 5 degrees and about 45 degrees.

In some configurations, the cushion includes a smooth transition in thickness between the at least one thin region and an adjacent portion of the face contacting portion. In some configurations, the transition is substantially linear.

In some configurations, a thickness of the at least one thin region is between about 5 percent and about 80 percent of a thickness of an adjacent portion of the face contacting portion. In some configurations, the thickness of the at least one thin region is between about 10 percent and about 30 percent of the thickness of the adjacent portion of the face contacting portion.

In some configurations, end portions of the at least one thin region are rounded.

In some configurations, the inner end portion of the at least one thin region is spaced outwardly from the inner edge of the face contacting portion.

In some configurations, the outer end portion of the at least one thin region is spaced inwardly from the outer edge of the face contacting portion.

In some configurations, the tube is a feeding tube.

In some configurations, the cushion comprises a visual alignment indicator that indicates a proper location of the tube.

In some configurations, a patient interface includes a cushion comprising a face contacting portion and at least one thin region at least partially within the face contacting portion. The thin region is adapted to accommodate the placement of a tube between the face contacting portion and a face of a user.

In some configurations, the cushion is adapted to create a seal around the user's nose and/or mouth.

In some configurations, the cushion is configured such that an upper portion of the cushion can be deflected forward relative to a lower portion of the cushion.

In some configurations, a headgear retains the patient interface on the head of a user. In some configurations, a frame portion interfaces with the headgear and the cushion interfaces with the frame portion.

In some configurations, the cushion comprises a relatively soft portion defining the face contacting portion and a relatively rigid portion facing away from the relatively soft portion.

In some configurations, the at least one thin region is located on a lateral side of the face contacting portion.

In some configurations, the at least one thin region comprises a thin region on each lateral side of the face contacting portion.

In some configurations, the at least one thin region comprises two or more thin regions on one lateral side of the face contacting portion.

In some configurations, the at least one thin region extends downwardly relative to a horizontal axis from an inner end portion to an outer portion.

In some configurations, the cushion includes a smooth transition in thickness between the at least one thin region and an adjacent portion of the face contacting portion.

In some configurations, a thickness of the at least one thin region is between about 5 percent and about 80 percent of a thickness of an adjacent portion of the face contacting portion. In some configurations, the thickness of the at least one thin region is between about 10 percent and about 30 percent of the thickness of the adjacent portion of the face contacting portion.

In some configurations, the patient interface includes a visual alignment indicator that indicates a proper location of the tube.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

In circumstances where NG, NJ and/or OG tubes are used in combination with NIV masks, undesirably high leak rates are a common occurrence. Having high leak rates can compromise the quality of therapy that a patient receives and the methods currently used to remedy the leaks can result in undesirable side-effects. Certain features, aspects and advantages of the disclosed embodiments seek to provide a useful alternative to currently known approaches of addressing and reducing these leaks.

The following description of certain features, aspects and advantages of certain embodiments refers to respiratory masks designed and configured to be used, or adapted for use, in combination with an NG tube; however, it is to be understood that the mask also can be used in combination with an NJ tube, both an NG tube and an NJ tube, which is more common, or any combination of an NJ tube, NG tube or OG tube. The respiratory masks can also be used, or adapted for use, with other types of tubes that are desired to pass between the mask cushion or seal and the patient's skin. Therefore, references to NG tubes herein can also refer to NJ tubes, OG tube, other tubes (e.g., fluid draining tubes) or any combination of NG tubes, NJ tubes, OG tube and other tubes.

The illustrated respiratory masks are NIV masks; however, the features, aspects and advantages described herein can be applied to other types of masks, as well. Certain features, aspects and advantages of the present masks are described in relation to providing therapy to adults; however, it also is possible to apply certain features, aspects and advantages of the present disclosure to respiratory masks for any age group, including but not limited to neonatal, infant and pediatric patients.

Figure 1:
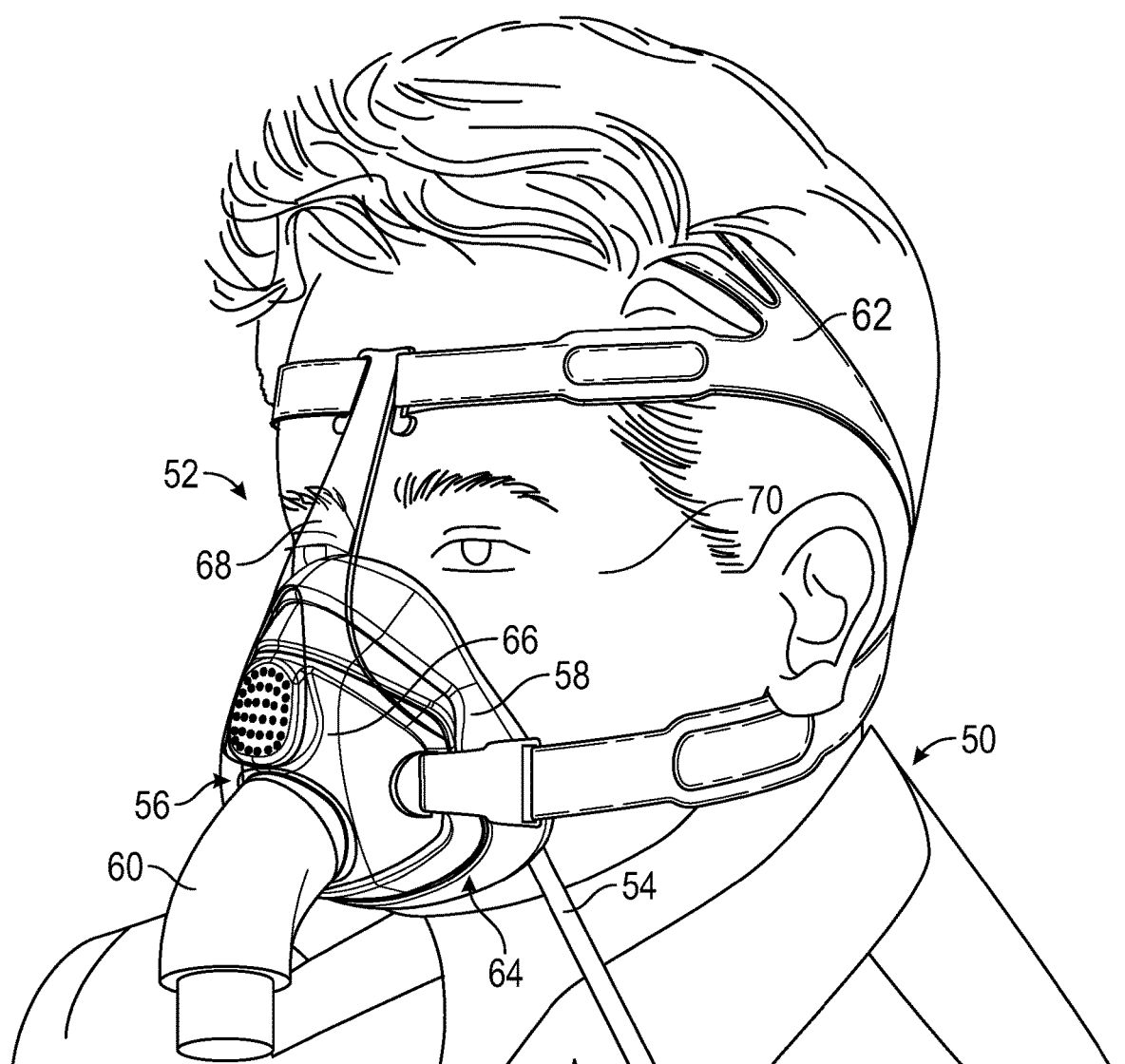
FIG. 1 shows a view of a patient wearing a respiratory mask (e.g., an NIV mask) arranged and configured in accordance with certain features, aspects and advantages of the present disclosure in combination with a tube (e.g., an NG tube) that extends down and out of the lower left side of the mask as viewed by the patient.

FIG. 1 illustrates a user or patient 50 wearing a respiratory (e.g., NIV) mask 52 in combination with an NG tube 54. The illustrated mask 52 includes a mask body or interface 56, which includes a cushion or seal 58 that contacts the user's face and surrounds the user's nose and/or mouth. The interface 56 also includes or is connected to a conduit connector 60 that allows the interface 56 to be connected to one or more gases conduits (not shown). In the illustrated arrangement, the conduit connector 60 is in the form of an elbow. A headgear 62 is coupled to the interface 56 and retains the interface 56 in position on the user's face.

The interface 56, conduit connector 60 and headgear 62 can take on many different forms. For example, the interface 56 can be a nasal interface, which covers only the user's nose, or a full face interface, which covers both the nose and mouth. Although a full face interface 56 is illustrated, the present disclosure can apply to other interface types in which a tube is desired to be passed between the interface cushion or seal and the user's face. The interface 56 can include or omit a forehead rest. In addition, the interface 56 (and, in some arrangements, the conduit connector 60) can be a one-piece structure or, as illustrated, can be an assembly of several components. The illustrated interface 56 includes a cushion module 64, which in some configurations includes a relatively rigid housing 66 and the relatively soft seal 58. The interface 56 also includes a frame 68, which can support the cushion module 64 and can provide connection or anchor locations for the headgear 62. The headgear 62 can be of any suitable arrangement, including single loop or multi loop arrangements.

It is typical for the NG tube 54 to be run from the nose towards the cheek and out the side of the mask 52. In a conventional mask, as illustrated by the dashed lines in FIG. 2, this arrangement can result in the formation of gaps between the mask seal and a corresponding surface of the user's face 70. While flexible, the conventional cushion is not capable of conforming to the geometry of the tube 54 to a degree necessary to prevent undesirably high rates of gas leakage through the gaps between the cushion and the user's face 70. Instead, a relatively large length of the cushion lifts away from the user's face 70 and curves over the tube 54 leaving gaps on either side of the tube 54 where leaks can occur. In general, the larger the diameter of the NG tube 54, the larger the size of the gaps.

Certain features, aspects and advantages of the present embodiments seek to reduce the gaps that form between the mask cushion 58 and the surface of the user's face 70 when an NG tube 54 is used by providing a conformable or compliant region 72 in the mask cushion 58 that can conform to the NG tube 54 to a degree sufficient to create or maintain an adequate seal with the user's face 70. The conformable or compliant region 72 can be of any suitable arrangement to increase the conformability or compliance of a portion of the cushion 58 relative to adjacent or surrounding portions of the cushion 58. As described herein, the conformable or compliant region 72 can be or comprise a region of thinned material or a region of different material, among other possible arrangements.

Preferably, the conformable or compliant region 72 can allow the present cushion 58 to create or maintain a better seal with the user's face 70 than a conventional mask cushion. In some configurations, the present cushion 58 can accommodate an NG tube 54 with less gas leakage between the cushion 58 and the user's face 70 in comparison to a conventional cushion. In some configurations, the present cushion 58 can accommodate an NG tube 54 with no or substantially no gas leakage between the cushion 58 and the user's face 70 or gas leakage that is below a rate considered to be detrimental to the prescribed therapy. In some configurations, the leak rate with the present cushion 58 accommodating an NG tube 54 within the conformable or compliant region 72 is equal to or less than about 25 L/min at a normal pressure or flow rate range for the prescribed (e.g., NIV) therapy. In some configurations, the leak rate is less than about 20 L/min, less than about 15 L/min or less than about 10 L/min.

Figure 2:
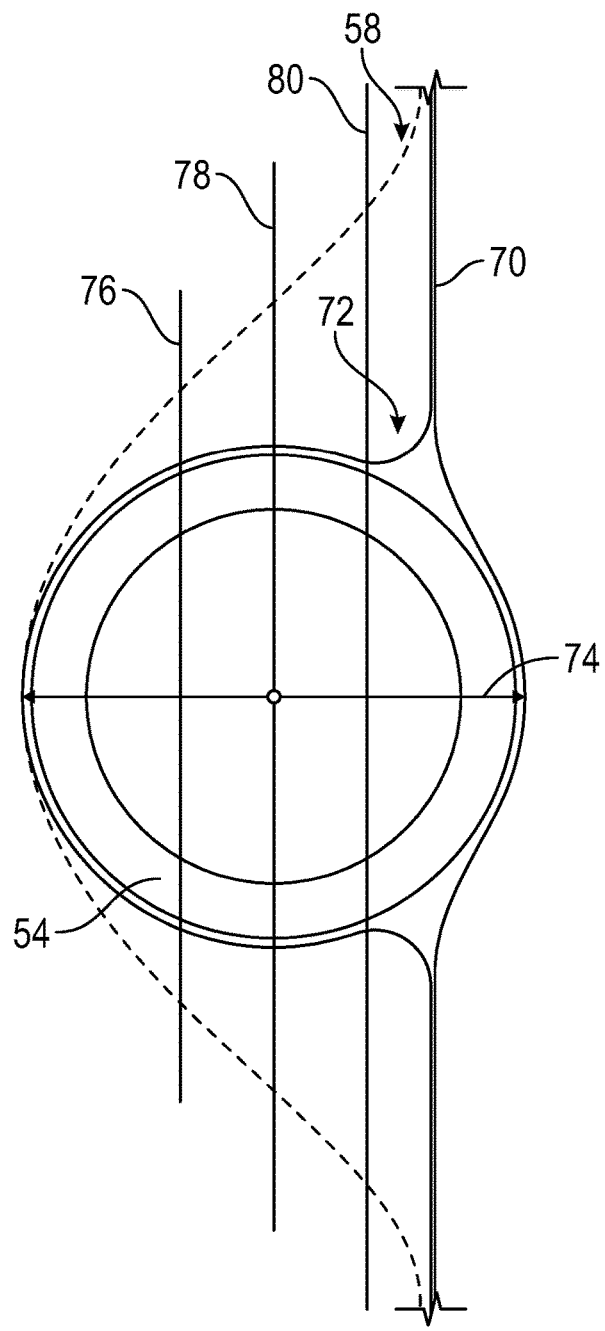
FIG. 2 is a profile view of a seal or cushion of the mask of FIG. 1 adapting or conforming to an NG tube in comparison to a regular mask shown in dashed line.

FIG. 2 illustrates a profile view of an NG tube 54 passing between the cushion 58 and the user's face 70. The conformable or compliant region 72 creates a tube path that is more compliant and flexible than the surrounding or adjacent portions of the cushion 58. In some configurations, the conformable or compliant region 72 is more compliant and flexible than any other portion of the cushion 58. FIG. 2 illustrates how the conformable or compliant region 72 stretches and deforms around the tube 54, which results in much smaller gaps at the side of the tube 54 than a cushion not having the specially configured tube paths. The size of the gaps will be largely dependent on the tube size that is being used. In FIG. 2, it is evident that the mask cushion 58 does not lift away from the face 70 to accommodate the NG tube 54 to the same degree as a traditional mask cushion that does not include tube paths.

The NG tube 54 has a cross-sectional dimension or diameter 74 extending in a direction away from the user's face 70. Preferably, the conformable or compliant region 72 allows the cushion 58 to contact or conform to at least a substantial portion of the NG tube 54 that is not in contact with the user's face 70. In some configurations, the conformable or compliant region 72 allows the cushion 58 to remain in contact with or conform to at least the outer one-third 76 of the surface of the NG tube 54 that is opposite the user's face 70. In some configurations, the conformable or compliant region 72 allows the cushion 58 to remain in contact with or conform to at least the outer one-half 78 of the surface of the NG tube 54. In some configurations, the conformable or compliant region 72 allows the cushion 58 to remain in contact with or conform to at least the outer two-thirds 80 of the surface of the NG tube 54. In some configurations, the conformable or compliant region 72 allows the cushion 58 to remain in contact with or conform to a substantial entirety of the surface of the NG tube 54 that is not in contact with the user's face 70.

Figure 3:
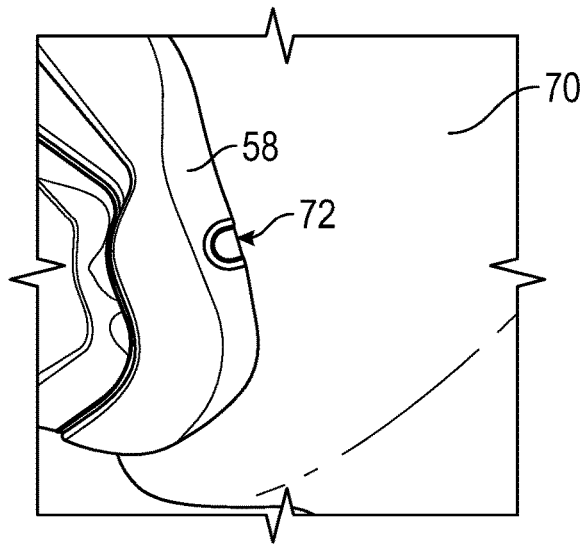
FIG. 3 is a profile view of the cushion of the mask of FIG. 1 with no NG tube present.

FIG. 3 illustrates a profile view of the mask cushion 58 of FIG. 2 being used without an NG tube 54. FIG. 3 illustrates that the conformable or compliant region 72 sits largely against and contacts the user's skin 70 when there is no NG tube 54 present. The external surface of the conformable or compliant region 72 can be shaped such that the conformable or compliant region 72 or tube path substantially follows the same contours as the rest of the mask cushion 58. Such a configuration helps the conformable or compliant region 72 to seal with the patient's face 70, which will create preferably no more than a negligible leak path in the absence of an NG tube 54. It is beneficial for the conformable or compliant region 72 to substantially follow the geometry of the rest of the cushion 58 because such a configuration will make the mask 52 more versatile and suitable for use on a wider range of users than otherwise possible. For example, the illustrated mask 52 can be used on any user or patient requiring NIV therapy, regardless of the need for use with tubes. Preferably, the patient-facing or contacting surface of the conformable or compliant region 72 and the patient-facing or contacting surface of the adjacent or surrounding portions of the cushion 58 define a continuous or uninterrupted surface. That is, preferably, there is no slit or other interruption in the patient-facing or contacting surface within or adjacent to the conformable or compliant region 72.

In some configurations, there may be a slight step in the external surface of the cushion 58. The slight step can be intentional or a result of the materials, configuration or manufacturing process used to create the conformable or compliant region 72. The step can be small enough that it will generate minimal leaks. The conformable or compliant region 72 may be flexible enough to inflate under the air pressure that is applied by the therapy such that the ballooning portion will fill any gaps that a step in the surface may otherwise cause.

As described above, the conformable or compliant region 72 can be of any suitable arrangement that provides for conformance to the type or size of the tube 54 or tubes intended for use with the mask 56. In some configurations, the conformable or compliant region 72 is substantially more conformable or compliant than surrounding or adjacent portions of the cushion 58. In some configurations, the increased conformability or compliance is at least partially the result of using a different material in the conformable or compliant region 72 relative to surrounding or adjacent portions of the cushion 58. For example, the increased conformability or compliance can be achieved through the localized use of a more elastic and flexible material. The different material can have a higher elasticity or different modulus of elasticity compared to the material of surrounding or adjacent regions of the cushion 58. Materials can include a different grade of silicone that is less hard or a more flexible TPE, for example but without limitation. In some configurations, the different material can also have a different thickness (e.g., less thickness) compared to the material of surrounding or adjacent regions of the cushion 58. The different material can be coupled to the material of surrounding or adjacent regions of the cushion 58 by any suitable process, which can include adhesive or chemical bonding or a co-molding or over-molding process, for example and without limitation, or any other appropriate method. In arrangements in which different material is utilized for the conformable or compliant region 72, the different material can extend beyond the conformable or compliant region 72. For example, such an arrangement can provide a greater surface area overlap for bonding of the two materials to one another.

In some configurations, the conformable or compliant region 72 is or comprises a region of thinned material. In the illustrated arrangements of FIGS. 4-8, the conformable or compliant region 72 comprises a region of thinned material that is the same material as the material of surrounding or adjacent regions of the cushion 58. Thus, the thinned material region can be unitarily formed with surrounding or adjacent regions of the cushion 58. Hereinafter, the conformable or compliant region 72 may be referred to as a thin region or thinned region. However, in view of the alternative structures for the conformable or compliant region 72, such references to a thin region can also generally include other types of conformable or compliant regions, as well. The conformable or compliant region 72 can define a tube path or tube paths that accommodate the passage of the NG tube 54 or other tubes between the cushion 58 and the user's face 70 and, thus, can also be referred to herein as a tube path. In some configurations, the tube path or tube paths 72 are formed to be thinner than the adjacent portions of the cushion 58. In some configurations, the tube path or tube paths 72 are formed to be thinner than any other portion of the cushion 58.

FIGS. 4-8 illustrate the cushion module 64 separate from other portions of the mask 52. As described, the cushion module 64 comprises the housing 66 and the seal or cushion 58. In the illustrated arrangement, the conformable or compliant region 72 of the seal 58 is or comprises a thin region. Preferably, the thin region 72 is defined by the seal wall, which thin region 72 is more capable of conforming to the tube 54 relative to surrounding, adjacent or other portions of the cushion 58. The cushion 58 generally has a patient face contacting portion or side 90 and a portion or side 92 forward of the face contacting portion 90. The face contacting portion 90 is generally rearward-facing and contacts the user's face 70. The face contacting portion 90 can deform when placed into contact with the user's face 70 and an entirety of the rearwardly-facing portion may not contact the face of all users or under all circumstances or therapies. In the illustrated configuration, an upper portion of the cushion 58 can be deflected forwardly relative to a lower portion of the cushion 58 to better accommodate variations in the nasal geometry of potential users. Examples of such an arrangement are disclosed in Applicant's PCT Publication No. WO2014/062070, the entirety of which is hereby incorporated by reference herein and made a part of the present disclosure. The cushion 58 can be made from one or more generally flexible materials, such as silicone or a TPE, for example but without limitation.

Figure 4:
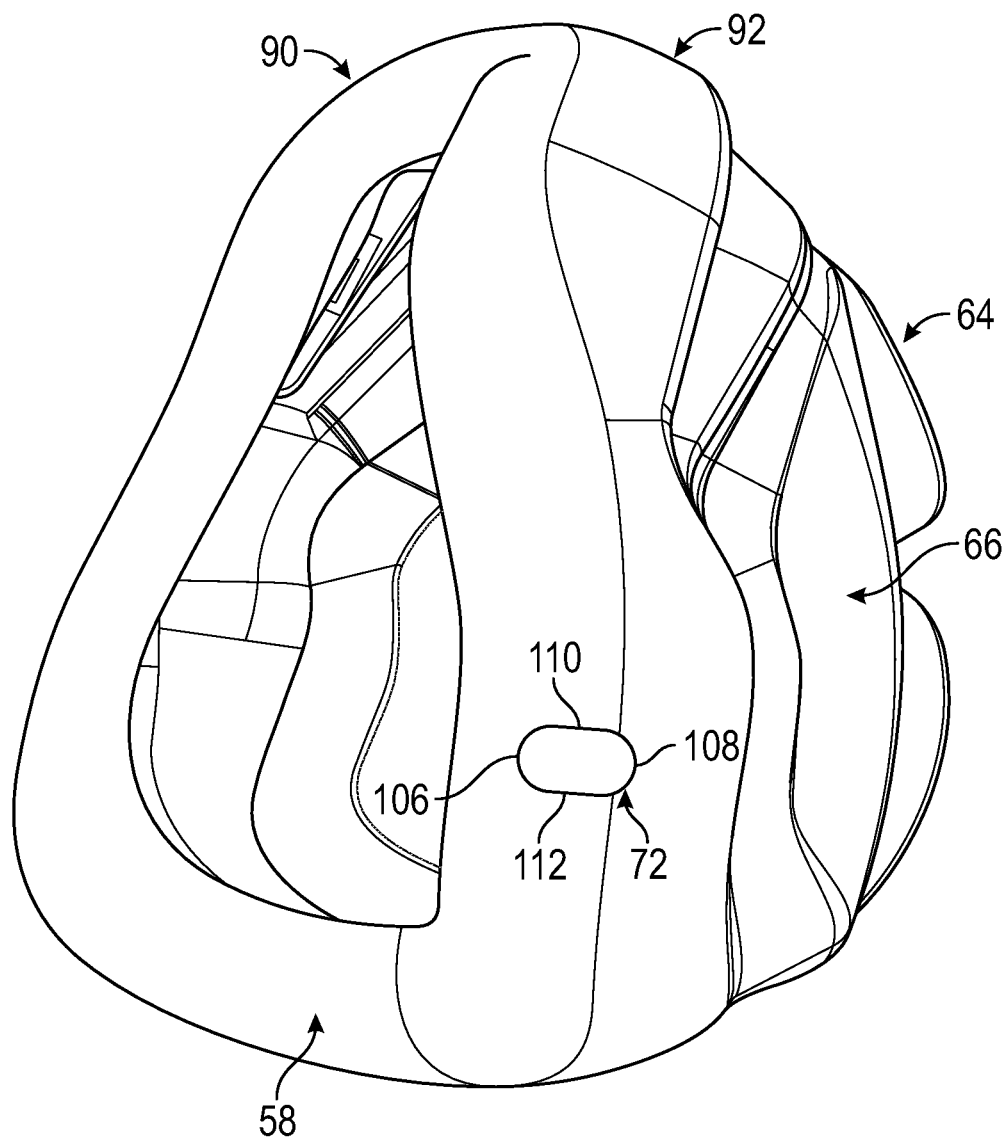
FIG. 4 is a perspective view of a portion of the mask of FIG. 1 illustrating a rounded profile of a thin region of the cushion.
Figure 5:
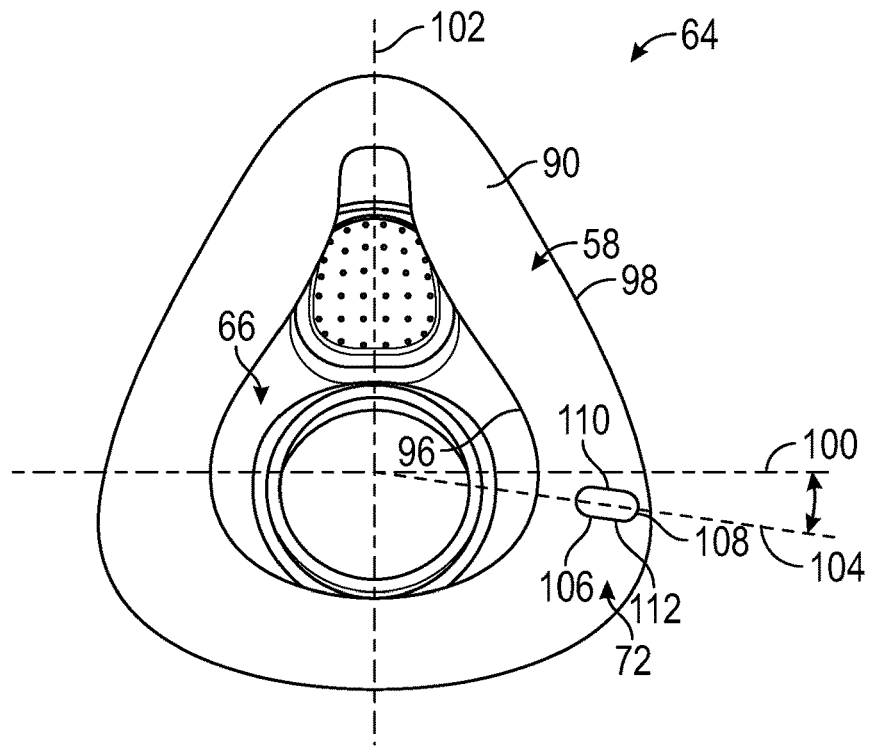
FIG. 5 is a rear view of a portion the mask of FIG. 1 illustrating an angled orientation of the thin region of the cushion.
Figure 6:
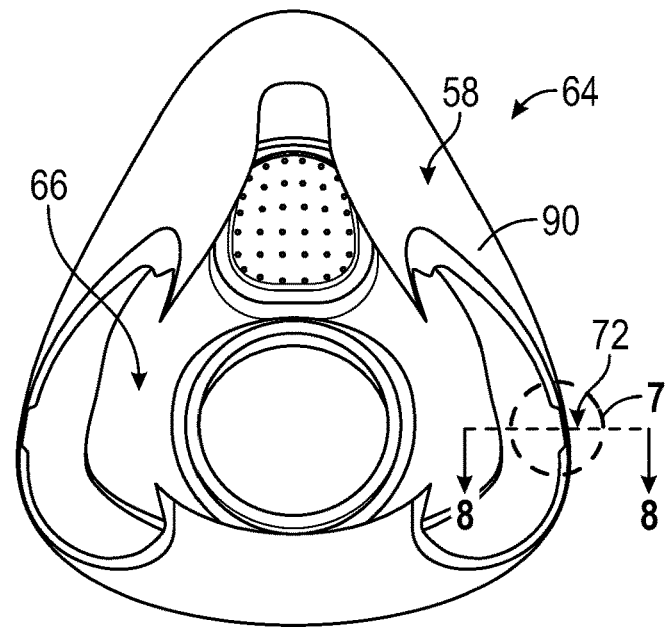
FIG. 6 is a rear view of a portion of the mask of FIG. 1 sectioned through a portion of the cushion containing the thin region.
Figure 7:
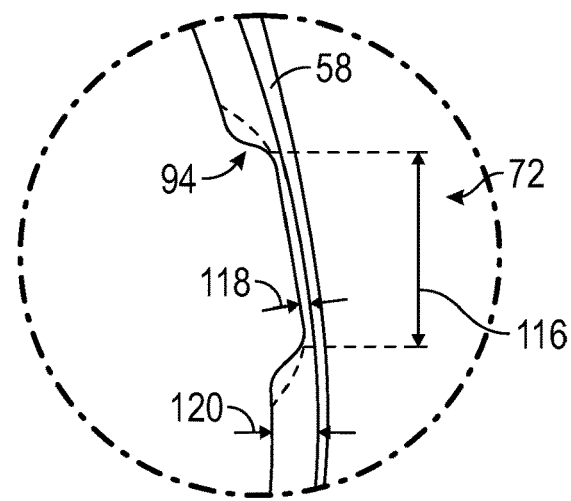
FIG. 7 is an enlarged view of the sectioned portion of the cushion containing the thin region of FIG. 6.
Figure 8:
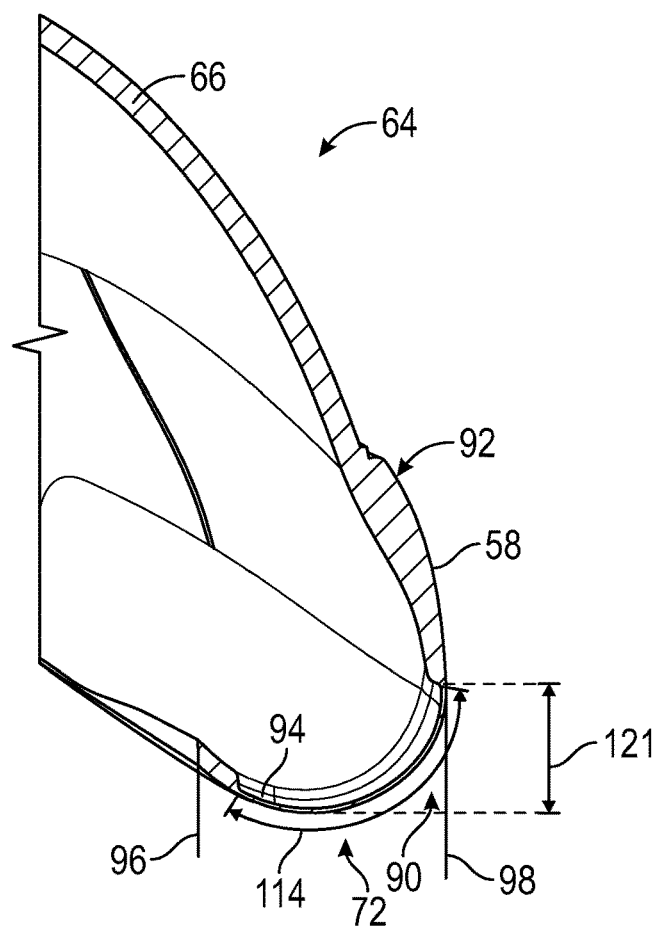
FIG. 8 is a sectioned view of the portion of the cushion containing the thin region taken along line 8-8 of FIG. 6.

A location of the thin region 72 is illustrated by an outline on an exterior surface of the cushion 58 in FIGS. 4 and 5. However, preferably, the thin region 72 is defined by a recess 94 defined by an interior surface of the cushion 58, as illustrated in FIGS. 6-8. The geometry of the thin region 72 can be configured or adapted to conform to a size or shape of the tube(s) intended for use with the mask 52. In some configurations, the thin region 72 can be positioned at least partially or entirely within the face contacting portion 90 of the cushion 58. With reference to FIG. 5, the thin region 72 extends generally in a direction from an inner edge 96 of the face contacting portion 90 towards an outer edge 98 of the face contacting portion 90. In some configurations, the thin region 72 can be spaced from one or both of the inner edge 96 and the outer edge 98. In some configurations, as illustrated in FIG. 4, the thin region 72 can extend beyond the outer edge 98 of the face contacting portion 90 and into the forward portion 92 of the cushion 58.

In some configurations, the thin region 72 is angled relative to a horizontal axis 100 of the cushion 58 or cushion module 64. A vertical axis 102 can bisect the cushion 58 or cushion module 64 in a vertical direction and the horizontal axis 100 is perpendicular to the vertical axis 102 and extends in a lateral direction of the cushion 58 or cushion module 64. An axis 104 of the thin region 72 and the horizontal axis 100 can define an angle therebetween of between about 5 degrees and about 45 degrees, or more if desired. In one configuration, the angle between the axis 104 and the horizontal axis 100 is about 20 degrees. In the illustrated arrangement, an inner end 106 of the thin region 72 closer to the centerline or vertical axis 102 is higher than an outer end 108 of the thin region 72 that is further from the centerline or vertical axis 102. Such an arrangement accommodates the typical path of the NG tube 54 as illustrated in FIG. 1. However, the thin region 72 can be provided in other orientations to suit other applications, as desired. For example, an oro-gastric (OG) tube may extend through the cushion 58 at about 0 degrees or generally along the horizontal axis 100. Thus, the specific orientation of the thin region 72 can be selected as desired in view of the particular tube, tube orientation or other relevant factors.

The thin region 72 can have any suitable size or shape to configured or adapted to conform to a size or shape of the tube(s) intended for use with the mask 52. In the illustrated arrangement, the thin region 72 defines substantially linear side edges 110 and 112 extending between the inner end 106 and the outer end 108. The side edges 110 and 112 can be substantially parallel to one another. The axis 104 can be defined as a line parallel to an equidistant from the side edges 110, 112. In some configurations, one or both of the inner end 106 and the outer end 108 can have a rounded or substantially semi-circular profile, as shown in FIGS. 4 and 5. This geometry will result in the thicker side-wall structure of the cushion 58 butting up to the circumference of the NG tube 54, and the thin region 72 deforming between the thicker side-wall and the tube 54. The thin region 72 can be thin enough to deform and stretch over an NG tube 54 for which the mask 52 is intended or approved for use without significantly lifting the cushion 58 away from the patient's face 70. In some configurations, no lift or substantially no lift will occur. The rounded geometry of the ends 106, 108 of the conforming region 72 can minimize the likelihood of the NG tube 54 being deformed or constricted by the relatively thicker adjacent wall portion of the cushion 58.

FIGS. 6-8 show cross-sectional views of the thin conforming region 72 of the cushion 58. In the illustrated configuration, the internal surface of the cushion 58 may reduce or step down from a relatively thicker wall section to the relatively thinner and more conformable portion 72 to define the interior recess 94 while the external surface can remain substantially unchanged. In other words, the external surface is continuous and uninterrupted between the thin region 72 and the adjacent or surrounding portions of the cushion 58. However, in some configurations, the external surface could include a recess in addition to or in the alternative to the internal recess 94 and ballooning a result of internal gas pressure could be relied on to create a seal with the user's face 70 in the absence of a tube 54.

The recess 94 can define a length 114 in a direction along the axis 104 and a height 116 in a direction perpendicular to the axis 104. The length 114 can be selected to extend along a length of the face contacting portion 90 that is likely to be in contact with the user's face 70 under typical or expected operating conditions. In some configurations, the length 114 is between about 15 mm and about 20 mm. The length 114 can vary with the size of the cushion 58 or can remain constant between different sized cushions 58. For example, the length 114 can vary from about 15.5 mm in a small cushion 58 to about 19 mm or 19.3 mm for a large cushion 58. The height 116 can be selected to accommodate the diameter or cross-sectional dimension of the tube(s) with which the mask 52 is designed or intended to be used. In some configurations, the height 116 is substantially equal to somewhat larger than the diameter of the maximum tube size with which the mask 52 is designed or intended to be used. In some configurations, the height 116 is between about 5 mm and about 15 mm, or between about 10 mm and 12 mm. The height 116 can vary with the size of the cushion 58, such as about 9 mm for an extra small cushion, about 10 mm for a small and medium cushion and about 11 mm for a large cushion. Alternatively, the height 116 can remain constant between cushion sizes.

The thin region 72 defines a wall thickness 118 that is less than a wall thickness 120 of portions of the cushion 58 adjacent to or surrounding the thin region 72. Preferably, the wall thickness 118 of the thin region 72 is less than the wall thickness 120. In some configurations, the wall thickness 118 is about 5 percent to about 80 percent or about 10 percent to about 30 percent of the wall thickness 120. In some configurations, the wall thickness 118 represents a reduction in thickness relative to the wall thickness 120 of between about 70 percent to about 95 percent, or about 80 percent to about 90 percent. For example, in some configurations, the wall thickness 120 can be about 1.49 or 1.5 mm and the wall thickness 118 can be between about 0.1 mm and about 0.5 mm, or between about 0.15 mm and about 0.3 mm.

In some configurations, the wall thickness 118 is about 0.3 mm. The wall thickness 118 within the recess 94 is illustrated as substantially constant (not including the transition portions between the recess 94 and the surrounding or adjacent portions of the cushion 58). However, in other arrangements, the wall thickness 118 can vary within the recess 94.

The cushion 58 can define a depth 121 (FIG. 8) in a forward-rearward direction from a rearward most point on the patient contacting portion 90 at a height of the thin region 72 and a location of the outer end 108 of the thin region 72. Having a sufficient depth 121 can assist the cushion 58 to remain in contact with the user's face 70 with an NG tube 54 in place. However, preferably, the depth 121 is not too large, or the thin region 72 does not extend too far toward or into the forward portion 92 of the cushion 58 to avoid unnecessary weakening of the cushion 58. The depth 121 can be related to the size of tube 54 with which the mask 52 is designed, intended or approved for use. In some configurations, the depth 121 is between about 10 mm and about 20 mm, or between about 15 mm and about 18 mm. The depth 121 can vary with the size of the cushion 58, such as about 14 mm or 14.3 mm for an extra small cushion, about 15.7 mm or about 16 mm for a medium cushion and about 17.8 mm or 18 mm for a large cushion. Alternatively, the depth 121 can remain constant between cushion sizes.

In some configurations, the transition in thickness between the recess 94 and the adjacent or surrounding portions of the cushion 58 can be relatively abrupt. The abrupt transition can create a fold point that restricts deformation that may be caused by a tube to the relatively thinner region 72 of the cushion 58. The relatively thinner region 72 can deform, stretch and/or bunch up until a relatively thicker wall portion is encountered, which can limit any further deformation. In other configurations, the transition in thickness can be less abrupt, as illustrated by the dashed lines at the edges of the recess 94 in FIG. 7. A smooth or less abrupt transition may be preferred for other reasons, such as manufacturability reasons, for example. Preferably, the transition is limited to a relatively small distance from the recess 94 or relatively small area surrounding the recess 94. For example, the transition can be substantially linear and/or can be an angle sufficient to allow the practical removal of a molded cushion 58 having the thin region 72 from a mold. In some configurations, the transition region preferably extends away from the thin region 72 a distance of no more than the width or length of the thin region 72 and, preferably, extends no more than a portion of the width or length of the thin region 72 (e.g., less than one-half, one-third or one-quarter of the width or length of the thin region 72).

Figure 9:
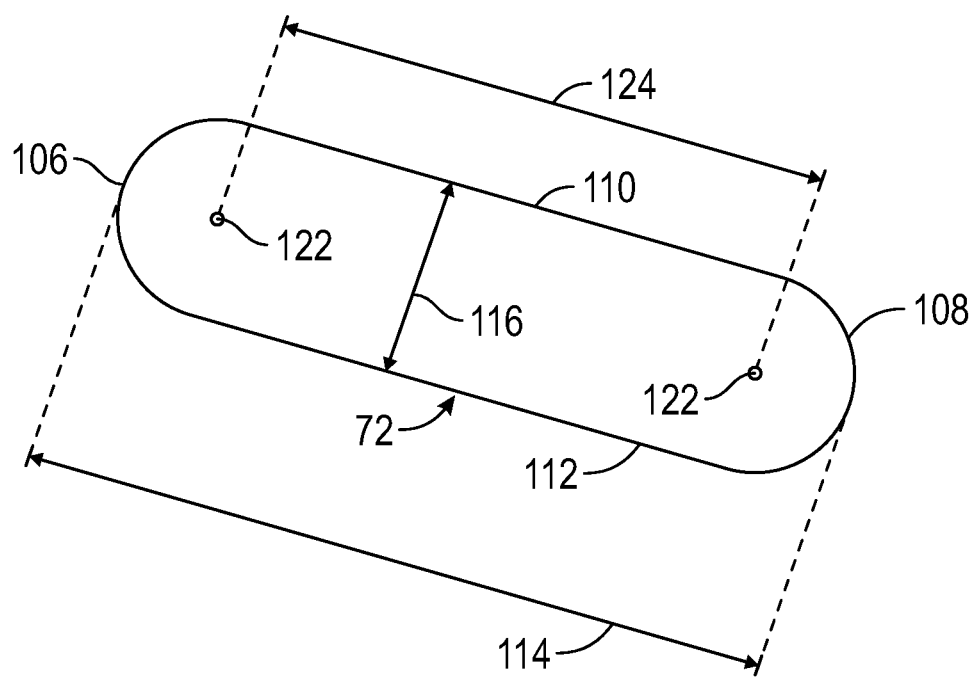
FIG. 9 is an outline of a shape of a thin region in a flattened condition.

FIG. 9 illustrates one example of an outline of a recess or thin region 72 in a flattened condition. In practice, the thin region 72 is likely to be curved or three-dimensional in shape because many patent contacting surfaces of mask cushions are curved in lateral and/or vertical directions. In FIG. 9, each end 106, 108 of the thin region 72 is semi-circular in shape about a respective center 122. Thus, a distance 124 between the centers 122 plus the radius of each end 106, 108 equals the overall length 114 of the thin region 72. In the illustrated thin region 72, the side edges 110, 112 are parallel to one another and each end 106, 108 is of an equal radius. However, in other arrangements, the thin region 72 can have other suitable shapes.

Figure 10:
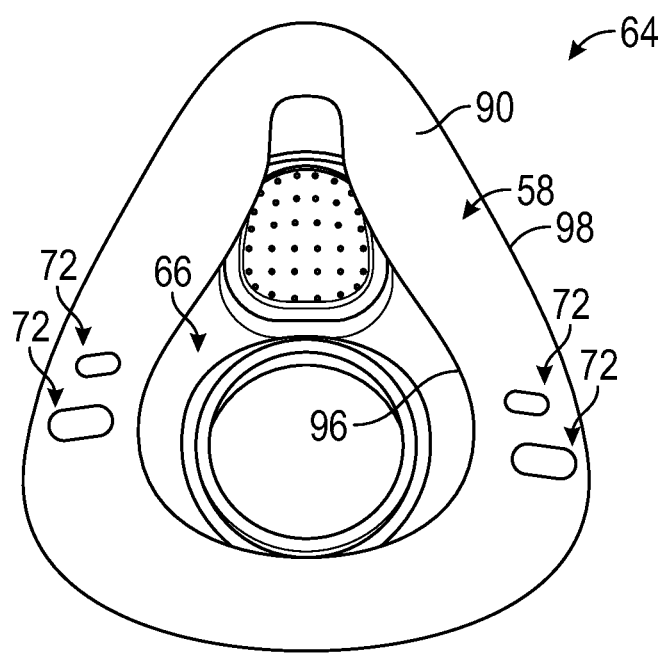
FIG. 10 is a rear view of a mask that shows a pair of thin regions on each side of the cushion, wherein the thin regions of the same side are differently sized and the thin regions are symmetrical between the sides.

In some configurations, such as that shown in FIG. 10, the conforming thin regions or tube paths 72 can be provided in multiple locations. FIG. 10 shows a rear view of the cushion 58 with two tube paths 72 spaced from one another along a perimeter of the cushion 58 and symmetrically located on each side of the mask 52. Having paths 72 on each side of the mask 52 allows for an NG tube 54 to be secured to either side of the patient's face 70. It is common practice for NG tubes 54 to be alternated between a patient's nostrils in order to reduce irritation and tissue damage within the nasal passage. Having symmetrical tube paths 72 on the mask 52 enables a clinician to change the side that the NG tube 54 is secured to and to continue to use the same mask 52. Such a configuration reduces wastage of equipment and may reduce work for the clinicians. Additionally, having tube paths 72 on both sides enables a cushion 58 to seal when both an NG tube 54 and an NJ tube are in simultaneous use.

Also shown in FIG. 10 are two different tube path 72 sizes. Because NG tubes 54 come in a variety of sizes, it is beneficial for the tube paths 72 to be able to conform to any size or at least commonly used sizes. It may be desired to have more than one path size in a mask 52 in order to cover a wider range of tube diameters with at least acceptable leak-rate performance. If a tube is too small for the tube path 72, the relatively thicker wall section of the cushion 58 may not be able to adequately restrict the deformation of the thin region 72 and gaps may form, which gaps can result in leaks. The size of the tube path 72 can be defined to suit a certain range of tube diameters. It is desirable for the round/circular profile of the tube path 72 to generally correlate to or match the tube diameter, as discussed above. By closely matching or generally correlating the tube path 72 to the tube 54, the relatively thicker wall section can force the thin region 72 to conform around the tube 54.

It is preferable not to have too many tube paths 72 or tube paths 72 that are too large because they can reduce the structural integrity of the cushion 58. The relatively thicker wall-section of the cushion 58 can be designed to provide structure and support to the mask 52. The cushion 58 can be provided with structure to reduce or eliminate the likelihood of the cushion 58 collapsing when the mask 52 is strapped on to a patient 50. If the cushion 58 collapses, leaks can occur and the rigid plastic mask frame 68 can be pushed against the patient's face 70 causing discomfort. Therefore, the number and size of tube paths 72 may be limited so that the structure of the cushion 58 is less likely to be compromised. The cushion 58 can include any single one or any combination of the tube paths 72 illustrated in FIG. 10, for example. In some configurations, the cushion 58 can include a single tube path 72 on one side or a single tube path 72 on each side. In configurations with at least one tube path 72 on each side, the tube paths 72 can be the same size or a different size. For example, the cushion 58 can include a relatively smaller tube path 72 on one side and a relatively larger tube path 72 on the other side. In some configurations, the cushion 58 includes a small and a large tube path 72 on each side.

Typically, NG tubes 54 are run from the underside of a patient's nose across their lip and out across the cheek. The tube 54 usually is secured to the nose with tape. The one or more tube paths 72 preferably are located on the cushion 58 such that they align approximately with the lower surface of a patient's nose or somewhat lower so that the tubes 54 can be secured to the patient 50 in approximately the conventional location for ease of use by the clinician. It can be beneficial for the tube 54 to be positioned over the soft part of a patient's cheek, anywhere below the zygomatic bone, to minimize the occurrence of pressure sores. Having the tube paths 72 located in such a way on the cushion 58 will enable clinicians to continue using traditional techniques for fitting and securing NG tubes 54. In some configurations, the tube paths 72 are located in the lower half of the cushion 58 or the lower third of the cushion 58. The tube paths 72 can be located at, near or somewhat above a widest point of a full face cushion 58. In some configurations, the tube paths 72 are spaced above a lowermost point of an inner edge of the cushion 58.

Figure 11A:
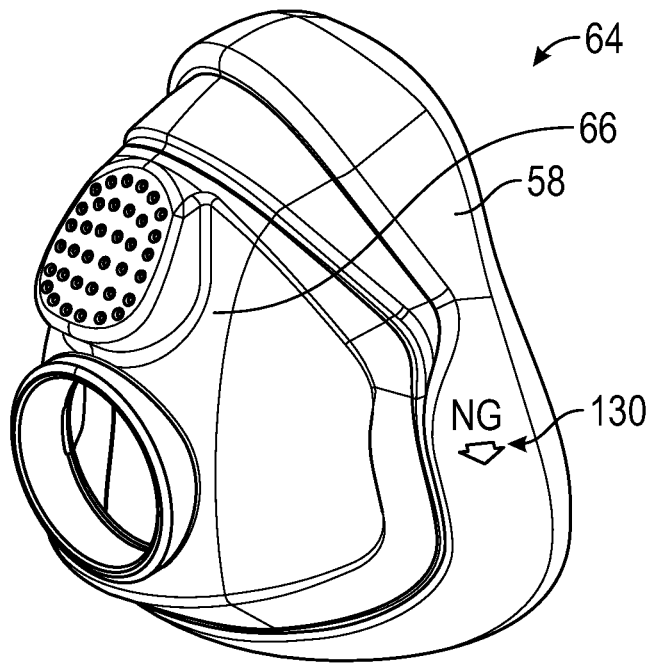
FIGS. 11A and 11B are perspective views of portions of two different masks having different types of visual alignment indicators to facilitate positioning of the tube relative to the cushion.
Figure 11B:
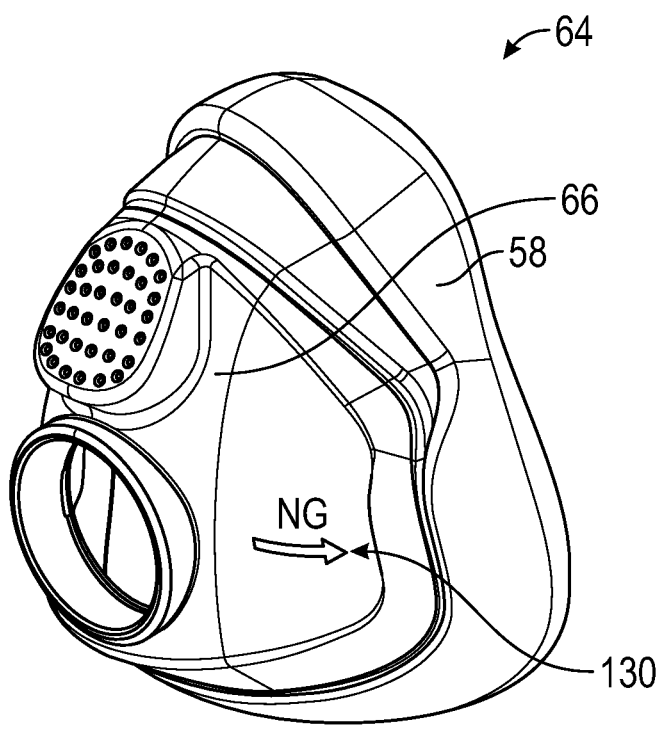

FIGS. 11A and 11B show embodiments of a cushion module 64 of a mask 52 having visual alignment indicators 130. The indicators 130 are intended to provide clinicians with a visual cue for aligning a mask 52 over the top of an NG tube 54 on a patient's face 70. For the illustrated masks 52 to work effectively, it is desirable for the NG tube 54 to be aligned accurately with respect to the tube paths 72 on the mask cushion 58. Misalignment may result in increased leak rates. The alignment indicators 130 can be in the form of an arrow and label that point towards the NG tube path 72. The indicator 130 may be located on the cushion 58, as illustrated in FIG. 11A, or the mask body (e.g., housing 66 or frame 68), as illustrated in FIG. 11B, proximate to the tube path 72. Embossing, printing, laser etching, molding or other marking techniques can be used to form the indicator 130 on the mask 52.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features or elements are in any way required for one or more embodiments.

The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A cushion for a respiratory mask, comprising:
    a face contacting portion configured to contact a face of a user and surround at least a portion of a nose and/or a mouth of the user;
    at least one conformable or compliant region configured to be more compliant and flexible than surrounding or adjacent portions of the cushion such that the at least one conformable or compliant region stretches and deforms around a tube, wherein the at least one conformable or compliant region is configured to accommodate placement of the tube between the face contacting portion and a face of the user; and
    an opening defined by an inner edge of the face contacting portion, the opening comprising an uppermost extent and a lowermost extent;
    wherein there is no slit or other interruption in the face contacting portion within or adjacent to the at least one conformable or compliant region,
    wherein an entirety of the at least one conformable or compliant region is located in a portion of the face contacting portion defined by the uppermost extent to the lowermost extent of the opening,
    wherein the at least one conformable or compliant region comprises a first material and the surrounding or adjacent portions of the cushion comprise a second material.

2. The cushion of claim 1, wherein the at least one conformable or compliant region comprises a thin region.

3. The cushion of claim 2, further comprising a smooth transition in thickness between the at least one thin region and an adjacent portion of the face contacting portion.

4. The cushion of claim 3, wherein the smooth transition is substantially linear.

5. The cushion of claim 2, wherein a thickness of the at least one thin region is between 5 percent and 80 percent of a thickness of an adjacent portion of the face contacting portion.

6. The cushion of claim 5, wherein the thickness of the at least one thin region is between 10 percent and 30 percent of the thickness of the adjacent portion of the face contacting portion.

7. The cushion of claim 1, wherein, in use, the at least one conformable or compliant region is configured to conform to a shape of the tube while maintaining an adequate seal with the face of the user.

8. The cushion of claim 1, wherein the at least one conformable or compliant region is located on a lateral side of the face contacting portion.

9. The cushion of claim 1, wherein the at least one conformable or compliant region comprises a first conformable or compliant region on a first lateral side of the face contacting portion and a second conformable or compliant region on a second lateral side of the face contacting portion.

10. The cushion of claim 9, wherein the first conformable or compliant region is larger than the second conformable or compliant region.

11. The cushion of claim 1, wherein the at least one conformable or compliant region comprises two or more conformable or compliant regions on one lateral side of the face contacting portion.

12. The cushion of claim 11, wherein a first conformable or compliant region and a second conformable or compliant region of the two or more conformable or compliant regions are spaced apart from one another.

13. The cushion of claim 12, wherein the first conformable or compliant region and the second conformable or compliant region are spaced apart along a perimeter of the face contacting portion.

14. The cushion of claim 11, wherein the two or more conformable or compliant regions comprise at least one larger conformable or compliant region and at least one smaller conformable or compliant region.

15. The cushion of claim 1, wherein the at least one conformable or compliant region extends in a direction from an inner edge of the face contacting portion toward an outer edge of the face contacting portion.

16. The cushion of claim 1, wherein the at least one conformable or compliant region extends downwardly relative to a horizontal axis of the cushion from an inner end portion of the cushion to an outer end portion of the cushion.

17. The cushion of claim 16, wherein the at least one conformable or compliant region extends downwardly at an angle of between 5 degrees and 45 degrees.

18. The cushion of claim 1, wherein each of the at least one conformable or compliant region comprise end portions that are rounded.

19. The cushion of claim 1, wherein an inner end portion of the at least one conformable or compliant region is spaced outwardly from an inner edge of the face contacting portion.

20. The cushion of claim 1, wherein an outer end portion of the at least one conformable or compliant region is spaced inwardly from an outer edge of the face contacting portion.

21. The cushion of claim 1, wherein the cushion is adapted to create a seal around the nose and/or mouth of the user.

22. The cushion of claim 1, wherein the cushion is configured such that an upper portion of the cushion can be deflected forward relative to a lower portion of the cushion.

23. The cushion of claim 1, wherein an external surface of each of the at least one conformable or compliant region can be shaped such that each of the at least one conformable or compliant region substantially follows the same contours as a remainder of the cushion.

24. The cushion of claim 1, wherein the face contacting portion of the at least one conformable or compliant region and the face contacting portion of the surrounding or adjacent portions of the cushion define a continuous or uninterrupted surface.

25. The cushion of claim 1, wherein the first material is different than the second material such that the first material is more conformable or compliant than the second material.

26. The cushion of claim 25, wherein the first material has a higher elasticity or different modulus of elasticity compared to the second material.

27. The cushion of claim 1, wherein the first material and the second material comprise thermoplastic elastomers.

28. A patient interface, comprising:
   the cushion of claim 1.

* * * * *